(12) United States Patent
Liu et al.

(10) Patent No.: US 11,553,657 B2
(45) Date of Patent: Jan. 17, 2023

(54) METHOD AND COMPOSITION FOR REGULATING PLANT ARCHITECTURE

(71) Applicant: CH Biotech R&D Co., Ltd., Nantou (TW)

(72) Inventors: Yu-Lun Liu, Nantou (TW); Cho-Chun Huang, Nantou (TW); Gui-Jun Li, Nantou (TW); Kai Xia, Nantou (TW)

(73) Assignee: CH BIOTECH R&D CO., LTD., Nantou (TW)

( * ) Notice: Subject to any disclaimer, the term of this patent is extended or adjusted under 35 U.S.C. 154(b) by 0 days.

(21) Appl. No.: 17/340,295

(22) Filed: Jun. 7, 2021

(65) Prior Publication Data

US 2022/0386546 A1 Dec. 8, 2022

(51) Int. Cl.
*A01H 3/04* (2006.01)
*A01N 33/04* (2006.01)
*A01N 37/44* (2006.01)

(52) U.S. Cl.
CPC ............... *A01H 3/04* (2013.01); *A01N 33/04* (2013.01); *A01N 37/44* (2013.01)

(58) Field of Classification Search
None
See application file for complete search history.

(56) References Cited

FOREIGN PATENT DOCUMENTS

CN 102608307 A * 7/2012

* cited by examiner

*Primary Examiner* — Alton N Pryor
(74) *Attorney, Agent, or Firm* — Locke Lord LLP; Tim Tingkang Xia, Esq.

(57) ABSTRACT

A method for regulating plant architecture includes applying a composition containing γ-Aminobutyric acid (GABA), glutamic acid and choline chloride to a plant. The composition for regulating plant architecture is also provided.

20 Claims, 5 Drawing Sheets

METHOD AND COMPOSITION FOR REGULATING PLANT ARCHITECTURE

BACKGROUND OF THE INVENTION

1. Field of the Invention

The present invention relates to a method for regulating plant architecture, especially to a method including applying a composition containing γ-Aminobutyric acid (GABA), glutamic acid and choline chloride to a plant.

2. Description of the Prior Art

Potted plants, including foliage plants, flower plants, and fruit plants, are essential elements for urban green space and landscape. High-quality potted plants require the plants to be relatively short and less leggy and/or to have high leaf density and good leaf growth, decreased apical dominance, good lodging resistance, thick stems, high flower numbers, and/or high flower density. Therefore, it is important to regulate plant architecture for potted plants.

Topping and heading cut are physical methods for regulating plant architecture by removing the apical growing point of a plant to reduce apical dominance and increase growth of axillary buds. However, topping and heading are labor-intensive. These labor-intensive methods greatly increase production costs and are not suitable for large scale planting.

In addition to physical methods, there are varies chemical approaches to reducing plant height and/or increasing branching. Gibberellin biosynthesis inhibitors, such as ancymidol, chormequat chloride, and flurprimidol, are used to reduce stem elongation, resulting in more compact plants. Dikegulac sodium, which acts as a chemical pincher, is translocated to the shoot apical meristem and inhibits DNA synthesis, resulting in shoot apical meristem cell death and reduction of apical dominance. Ethephon, an ethylene-releasing agent, suppresses stem elongation and reduces apical dominance. In addition, 6-benzyladine, a cytokinin, is used to promote lateral bud outgrowth. However, these plant growth regulators often result in crop injury such as phytotoxicity and necrosis. Therefore, there is need for another method for regulating plant architecture and promoting plant branching.

SUMMARY OF THE INVENTION

In one aspect, the present invention relates to a concentrate composition for regulating plant architecture, comprising between about 5 to about 125 g/L γ-Aminobutyric acid (GABA), between about 20 to about 200 g/L glutamic acid, and between about 15 to about 375 g/L choline chloride.

In another aspect, the present invention relates to a ready to use composition for regulating plant architecture, comprising between about 10 to about 625 mg/L GABA, between about 40 to about 2,500 mg/L glutamic acid, and between about 30 to about 1,875 mg/L choline chloride.

In another aspect, the present invention relates to a method for regulating plant architecture, comprising a step of applying a use solution composition for regulating plant architecture to a plant, and the use solution composition for regulating plant architecture comprising between about 10 to about 625 mg/L GABA, between about 40 to about 2,500 mg/L glutamic acid, and between about 30 to about 1,875 mg/L choline chloride.

The present invention is illustrated but not limited by the following embodiments and drawings.

BRIEF DESCRIPTION OF THE DRAWINGS

FIG. 1A: Control group; FIG. 1B: Test group 1-1; FIG. 1C: Test group 1-2; and FIG. 1D: Test group 1-3.

FIG. 3A: Control group; FIG. 3B: Test group 1-1; FIG. 3C: Test group 1-2; and FIG. 3D: Test group 1-3.

FIG. 5A: Control group; FIG. 5B: Test group 2-1; FIG. 5C: Test group 2-2; and FIG. 5D: Test group 2-3.

DETAILED DESCRIPTION OF THE PREFERRED EMBODIMENT

Figure 1A:
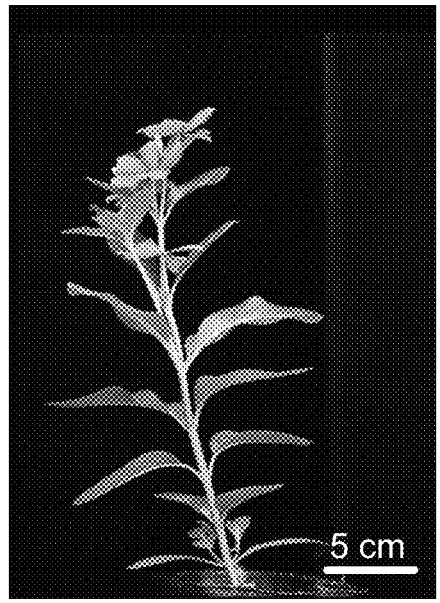
FIGS. 1A to 1D show phenotype observation of rosy periwinkle one week after the second application of reagents in Example 1.
Figure 1B:
Figure 1C:
Figure 1D:

The inventors of the present invention surprisingly found that when a composition comprising exogenous GABA, glutamic acid, and choline chloride is applied to a plant, the composition significantly regulates plant architecture, including increasing total branch number of the plant, reducing apical dominance, reducing branch length, increasing leaf density, increasing lodging resistance, increasing total flower number, increasing flower bud number, and/or increasing flower density.

Therefore, the present invention provides a composition for regulating plant architecture. In some embodiments, the composition for regulating plant architecture of the present invention is a concentrate composition, comprising between about 5 to about 125 g/L GABA, between about 20 to about 200 g/L glutamic acid, and between about 15 to about 375 g/L choline chloride. A concentrate solution refers to a solution which is intended to be diluted with water to form a use solution prior to application to the plant.

In some embodiments, the concentration of GABA in the concentrate composition for regulating plant architecture is between about 5 to about 125 g/L, between about 10 to about 100 g/L, between about 25 to about 50 g/L, and preferably is, but is not limited to, about 5 g/L, about 10 g/L, about 15 g/L, about 20 g/L, about 25 g/L, about 30 g/L, about 35 g/L, about 40 g/L, about 45 g/L, about 50 g/L, about 55 g/L, about 60 g/L, about 65 g/L, about 70 g/L, about 75 g/L, about 80 g/L, about 85 g/L, about 90 g/L, about 95 g/L, about 100 g/L, about 105 g/L, about 110 g/L, about 115 g/L, about 120 g/L, about 125 g/L, or any concentration between about 5 g/L to 125 g/L, such as about 17.65 g/L, about 61.47 g/L, or about 113.69 g/L. In some embodiments, the concentration of GABA in the concentrate composition for regulating plant architecture is about 10 g/L, about 25 g/L, about 50 g/L, about 100 g/L, or about 125 g/L.

In some embodiments, the concentration of glutamic acid in the concentrate composition for regulating plant architecture is between about 20 to about 200 g/L, between about 30 to about 175 g/L, between about 50 to about 150 g/L, and preferably is, but is not limited to, about 20 g/L, about 30 g/L, about 40 g/L, about 50 g/L, about 60 g/L, about 70 g/L, about 80 g/L, about 90 g/L, about 100 g/L, about 110 g/L, about 120 g/L, about 130 g/L, about 140 g/L, about 150 g/L, about 160 g/L, about 170 g/L, about 180 g/L, about 190 g/L, about 200 g/L, or any concentration between about 20 g/L to about 200 g/L, such as about 31.86 g/L, about 63.31 g/L, and about 103.63 g/L. In some embodiments, the concentration of glutamic acid in the concentrate composition for regulating plant architecture is about 20 g/L, about 50 g/L, about 75 g/L, about 100 g/L, about 125 g/L, about 150 g/L, about 175 g/L, or about 200 g/L.

In some embodiments, the concentration of choline chloride in the concentrate composition for regulating plant architecture is between about 15 to about 375 g/L, between about 30 to about 300 g/L, between about 50 to about 250 g/L, between about 75 to about 150 g/L, and preferably is, but is not limited to, about 15 g/L, about 50 g/L, about 75 g/L, about 100 g/L, about 125 g/L, about 150 g/L, about 175 g/L, about 200 g/L, about 225 g/L, about 250 g/L, about 275 g/L, about 300 g/L, about 325 g/L, about 350 g/L, about 375 g/L, or any concentration between about 15 g/L to about 375 g/L, such as about 48.61 g/L, about 76.19 g/L, and about 238.74 g/L. In some embodiments, the concentration of choline chloride in the concentrate composition for regulating plant architecture is about 15 g/L, about 75 g/L, about 150 g/L, about 250 g/L, or about 375 g/L.

In some embodiments, the concentrate composition for regulating plant architecture is diluted around 200 to 500 folds with water before use.

In some embodiments, the composition for regulating plant architecture of the present invention is a ready to use composition, comprising between about 10 to about 625 mg/L GABA, between about 40 to about 2500 mg/L glutamic acid, and between about 30 to about 1,875 mg/L choline chloride. A ready to use solution is not diluted with water prior to application to the plant. A ready to use solution is a use solution when it is applied to the plant without further dilution.

In some embodiments, the concentration of GABA in the ready to use composition for regulating plant architecture is between about 10 to about 625 mg/L, between about 50 to about 500 mg/L, between about 75 to about 300 mg/L, between about 100 to about 200 mg/L, and preferably is, but is not limited to, about 10 mg/L, about 50 mg/L, about 75 mg/L, about 100 mg/L, about 150 mg/L, about 200 mg/L, about 250 mg/L, about 300 mg/L, about 350 mg/L, about 400 mg/L, about 450 mg/L, about 500 mg/L, about 550 mg/L, about 600 mg/L, about 625 mg/L, or any concentration between about 10 mg/L to 625 mg/L, such as about 74.53 mg/L, about 103.74 mg/L, or about 329.65 mg/L. In some embodiments, the concentration of GABA in the ready to use composition for regulating plant architecture is about 10 mg/L, about 75 mg/L, about 100 mg/L, about 250 mg/L, about 500 mg/L, or about 625 mg/L.

In some embodiments, the concentration of glutamic acid in the ready to use composition for regulating plant architecture is between about 40 to about 2,500 mg/L, between about 100 to about 2,000 mg/L, between about 250 to about 1,000 mg/L, and preferably is, but is not limited to, about 40 mg/L, about 100 mg/L, about 200 mg/L, about 300 mg/L, about 400 mg/L, about 500 mg/L, about 600 mg/L, about 700 mg/L, about 800 mg/L, about 900 mg/L, about 1,000 mg/L, about 1,100 mg/L, about 1,200 mg/L, about 1,300 mg/L, about 1,400 mg/L, about 1,500 mg/L, about 1,600 mg/L, about 1,700 mg/L, about 1,800 mg/L, about 1,900 mg/L, about 2,000 mg/L, about 2,100 mg/L, about 2,200 mg/L, about 2,300 mg/L, about 2,400 mg/L, about 2,500 mg/L, or any concentration between about 40 mg/L to 2,500 mg/L, such as about 191.86 mg/L, about 1,203.31 mg/L, and about 2,403.63 mg/L. In some embodiments, the concentration of glutamic acid in the ready to use composition for regulating plant architecture is about 40 mg/L, about 100 mg/L, about 200 mg/L, about 400 mg/L, about 800 mg/L, about 1,200 mg/L, about 1,600 mg/L about 2,000 mg/L, or about 2,500 mg/L.

In some embodiments, the concentration of choline chloride in the ready to use composition for regulating plant architecture is between about 30 to about 1,875 mg/L, between about 100 to about 1,500 mg/L, between about 200 to about 1,000 mg/L, between about 300 to about 500 mg/L, and preferably is, but is not limited to, about 30 mg/L, about 100 mg/L, about 200 mg/L, about 300 mg/L, about 400 mg/L, about 500 mg/L, about 600 mg/L, about 700 mg/L, about 800 mg/L, about 900 mg/L, about 1,000 mg/L, about 1,100 mg/L, about 1,200 mg/L, about 1,300 mg/L, about 1,400 mg/L, about 1,500 mg/L, about 1,600 mg/L, about 1,700 mg/L, about 1,800 mg/L, about 1,875 mg/L, or any concentration between about 30 mg/L to 1,875 mg/L, such as about 117.65 mg/L, about 533.14 mg/L, and about 1,294.63 mg/L. In some embodiments, the concentration of choline chloride in the ready to use composition for regulating plant architecture is about 30 mg/L, about 100 mg/L, about 300 mg/L, about 500 mg/L, about 1,000 mg/L, about 1,500 mg/L, or about 1,875 mg/L.

In some embodiments, the composition for regulating plant architecture of the present invention may include one or more adjuvant. In other embodiments, the composition for regulating plant architecture of the present invention may not include an adjuvant. For example, the composition for regulating plant architecture may include a surfactant and/or a drift control agent. Exemplary surfactants include, but are not limited to, cationic surfactants, anionic surfactants, zwitterionic surfactants, and nonionic surfactants, preferably including but not limited to, Tween® 20, Tween® 40, Tween® 60, Tween® 65, Tween® 80, Tween® 85, Laureth-4, Ceteth-2, Ceteth-20, Steareth-2, PEG40, PEG100, PEG150, PEG200, PEG600, Span® 20, Span® 40, Span® 60, Span® 65, Span® 80. An exemplary drift control agent includes LI 700®, which is commercially available from Loveland Products (Loveland, Colo., USA).

In some embodiments, the concentration of the adjuvant in the ready to use composition for regulating plant architecture is between about 0.01 to 1% (v/v), and preferably is, but is not limited to, about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, about 1% (v/v). In some embodiments, the concentration of the adjuvant in the ready to use composition for regulating plant architecture is about 0.1% (v/v).

Suitable concentration ranges for the concentrate composition for regulating plant architecture of the present invention are provided in Table 1, and suitable concentration ranges for the ready to use composition for regulating plant architecture of the present invention are provided in Table 2. In some embodiments, the concentrate composition for regulating plant architecture and the ready to use composition for regulating plant architecture can comprise, consist of or consist essentially of the components listed in Table 1 and 2, respectively.

TABLE 1

Suitable concentrate composition for regulating plant architecture

| Component | First example range (g/L) | Second example range (g/L) | Third example range (g/L) |
| --- | --- | --- | --- |
| GABA | 2.5-250 | 5-125 | 10-50 |
| Glutamic acid | 10-200 | 20-200 | 40-150 |
| Choline chloride | 7.5-750 | 15-375 | 30-150 |

TABLE 2

Suitable ready to use composition for regulating plant architecture

| Component | First example range (mg/L) | Second example range (mg/L) | Third example range (mg/L) |
| --- | --- | --- | --- |
| GABA | 5-1,250 | 10-625 | 20-250 |
| Glutamic acid | 20-5,000 | 40-2,500 | 80-1000 |
| Choline chloride | 15-3,750 | 30-1,875 | 60-750 |

The present invention also provides a method for regulating plant architecture, comprising a step of applying a use solution composition for regulating plant architecture to a plant, and the use solution composition for regulating plant architecture comprising between about 10 to about 625 mg/L GABA, between about 40 to about 2,500 mg/L glutamic acid, and between about 30 to about 1,875 mg/L choline chloride.

In some embodiments, the plant may be a potted plant, such as, but is not limited to, a foliage plant, a flower plant, and a fruit plant.

In some embodiments, the composition for regulating plant architecture of the present invention is applied to a plant during the vegetative phase. In some embodiments, the composition for regulating plant architecture of the present invention is applied to a plant during the reproductive phase.

In some embodiments, the composition for regulating plant architecture of the present invention is applied to plant foliage (for example, leaves, stems, flowers and/or fruits), for example as a foliar application or foliar spray. In some embodiments, the composition for regulating plant architecture of the present invention is applied to plant roots, such as by a soil application or soil drench, and/or to seeds, such as by a seed treatment.

Unless otherwise defined, all technical and scientific terms used herein have the same meaning as commonly understood by one of ordinary skill in the art to which this invention pertains. In the case of conflict, the present document, including definitions will control.

As used herein, the term "γ-Aminobutyric acid (GABA)," also known as 4-aminobutanoic acid, refers to a non-protein amino acid having the formula of $C_4H_9NO_2$ and the following chemical structure:

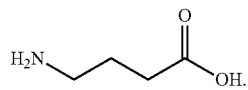

As used herein, the term "glutamic acid," also known as 2-aminopentanedioic acid, refers to an amino acid having the formula $C_5H_9NO_4$ and the following chemical structure:

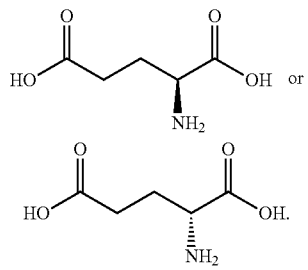

As used herein, the term "choline chloride" refers to an organic compound having the formula of $((CH_3)_3N(Cl)CH_2CH_2OH)$ and the following chemical structure:

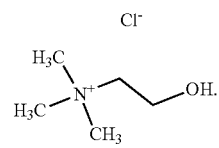

As used herein, the term "surfactants" refers to molecules with the chemical formula RCOOM, where R is a long-chain alkyl group and M is a base, and therefore, surfactants are molecules containing both lipophilic groups (the long-chain alkyl group) and hydrophilic groups, which allow oily substances to be dispersed or dissolved in water. The surfactants described herein include, but are not limited to, cationic surfactants, anionic surfactants, zwitterionic surfactants, and non-ionic surfactants, such as Tween® series, Laureth series, Ceteth series, Steareth series, PEG series, and Span® series.

As used herein, the term "regulating plant architecture" or "improving plant architecture" refers to that compared with plants without treatment of the composition of the present invention, plants treated with the composition of the present invention have at least one of following properties: more lateral bud differentiations, more branches, decreased apical dominance, are relatively short, are less leggy, better lodging resistance, higher leaf density, better leaf growth, thicker stems, more flowers, higher flower density.

As used herein, the term "apical dominance" refers to the phenomenon whereby the main, central stem of a plant grows more strongly than other side stems, or the terminal bud and shoot apex of a plant control over the outgrowth of lateral buds.

As used herein, the term "increasing branch number" or "increasing plant branches" refers to that compared with plants without treatment of the composition of the present invention, plants treated with the composition of the present invention have decreased apical dominance, and/or have increasing growth of lateral stems, branches, or lateral buds. There are two main types of plant branching, dichotomous branching and lateral or axillary branching. Lateral branching includes racemose or monopodial branching and cymose or sympodial branching; types of cymose branching include, but are not limited to, uniparous cymose branching, biparous cymose branching, and multiparous cymose branching.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "a," "an," or "the" disclosed in the present invention is intended to cover one or more numerical values in the specification and claims unless otherwise specified. For example, "an element" indicates one or more than one element.

It is to be understood that both the foregoing general description and the following detailed description are exemplary and explanatory only and are not restrictive of the invention.

EXAMPLES

Example 1 Rosy Periwinkle Test

1. Preparation of Test Plants

Seedlings of rosy periwinkle (*Catharanthus roseus*) were used as test plants in this example. Seeds of rosy periwinkle were collected in the field in Nantou City, Nantou County, Taiwan. Plants grown from the seeds were self-pollinated, and seeds from the self-pollinated plants were harvested. The harvested seeds were sown in pots containing culture medium (peat soil:vermiculite=3:1).

2. Plant Treatment

Rosy periwinkle seedlings with two sets of unfolded true leaves were applied with the reagents listed in Table 3 twice with a two-week interval, using a foliar spray treatment. Plants in control group were applied with 0.1% (v/v) Tween® 80 in distilled water. The plants were kept in the phytotron until flowering stage for further analysis. Each group had 12 plants (n=12).

TABLE 3

Summary of the reagents applied to rosy periwinkle in Example 1.

| Group | GABA (mg/L) | Glutamic acid (mg/L) | Choline chloride (mg/L) | Tween ® 80 |
|---|---|---|---|---|
| Control group | 0 | 0 | 0 | 0.1% (v/v) |
| Test group 1-1 | 100 | 0 | 0 | 0.1% (v/v) |
| Test group 1-2 | 0 | 400 | 300 | 0.1% (v/v) |
| Test group 1-3 | 100 | 400 | 300 | 0.1% (v/v) |

3. Analyses 3.1 Plant morphology: Plant morphology was observed one week after the second application of reagents.

3.2 Total branch number: The total branch number of each plant was calculated one week after the second application of reagents. This test was run in triplicate.

3.3 Total flower bud number: The total flower bud number of each plant was calculated one week after the second application of reagents. The total flower bud number represents the sum of the flower buds having a length greater than 0.5 cm. This test was run in triplicate.

3.4 Statistical analyses: Average and standard deviation (S.D.) of each group (n=12) were calculated. Statistically significant differences between control group and test groups were assessed by Student's T-test, where p-value<0.05 was considered a significant difference and indicated by an asterisk (*). The p-value<0.01 was considered a highly significant difference. ** p<0.01.

4. Results 4.1 Plant morphology: The plant morphology of Control group, Test groups 1-1, 1-2, and 1-3 are shown in FIGS. 1A, 1B, 1C, and 1D, respectively. Compared with plants of Control group, plants treated with GABA only (Test group 1-1), and plants treated with choline chloride and glutamic acid only (Test group 1-2), plants treated with the composition of the present invention (Test group 1-3) have significantly more branches and better plant architecture one week after the second application of reagents.

Figure 2:
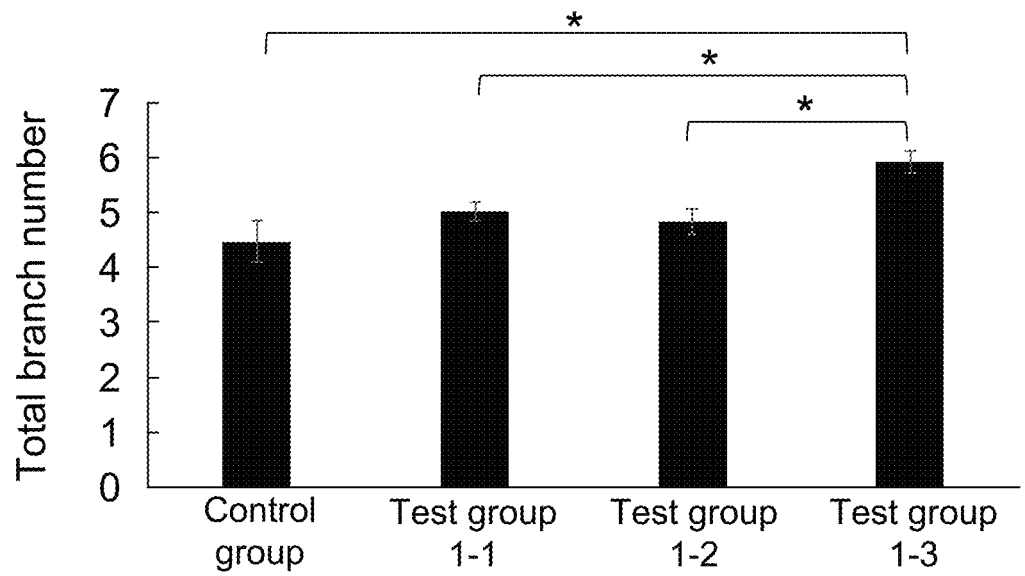
FIG. 2 shows the total branch numbers of rosy periwinkle one week after the second application of reagents in Example 1. * $p<0.05$.

4.2 Total branch number: As shown in FIG. 2, plants treated with the composition of the present invention (Test group 1-3) have greater total branch number than plants of Control group, plants treated with GABA only (Test group 1-1), and plants treated with choline chloride and glutamic acid only (Test group 1-2). There are significant differences between Test group 1-3 and Control group, between Test group 1-3 and Test group 1-1, and between Test group 1-3 and Test group 1-2 (p<0.05).

Figure 4:
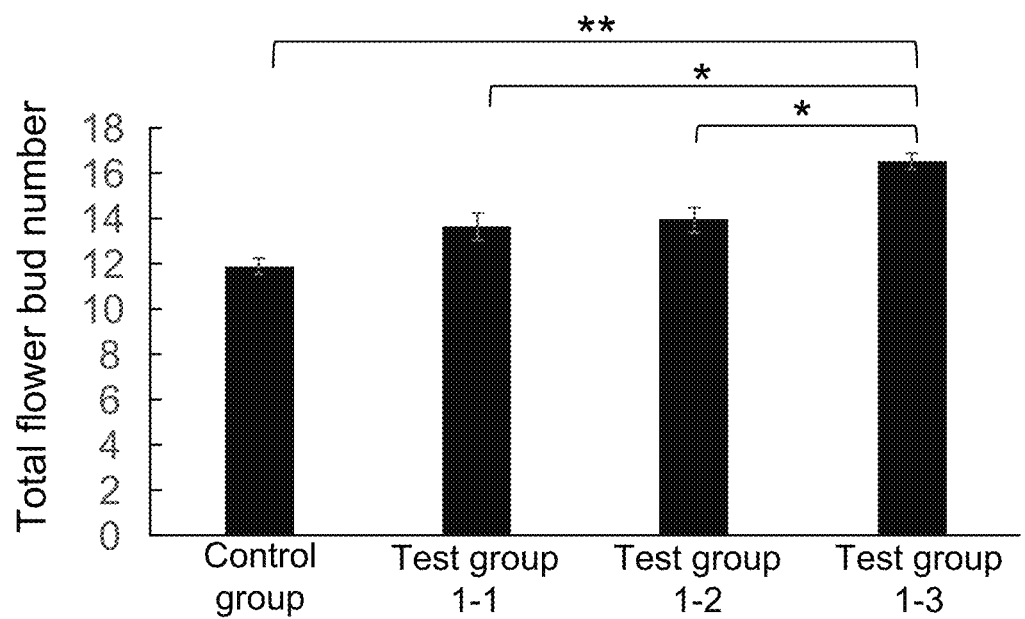
FIG. 4 shows the total flower bud numbers of rosy periwinkle one week after the second application of reagents in Example 1. * $p<0.05$ and ** $p<0.01$.
Figure 3A:
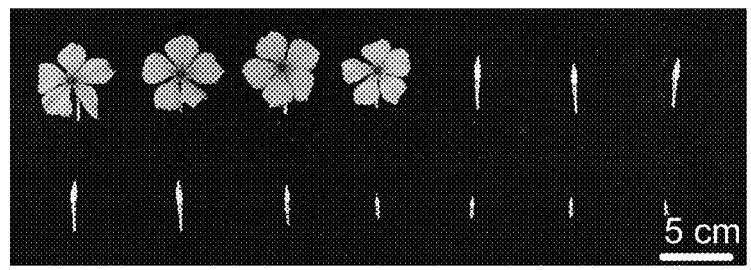
FIGS. 3A to 3D show phenotype observation of flower buds of rosy periwinkle one week after the second application of reagents in Example 1.
Figure 3B:
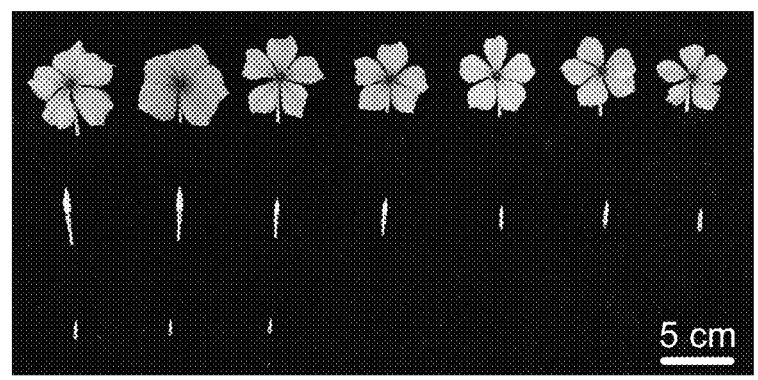
Figure 3C:
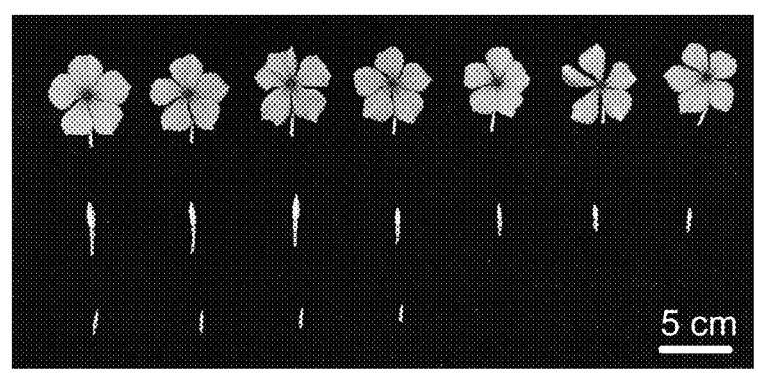
Figure 3D:
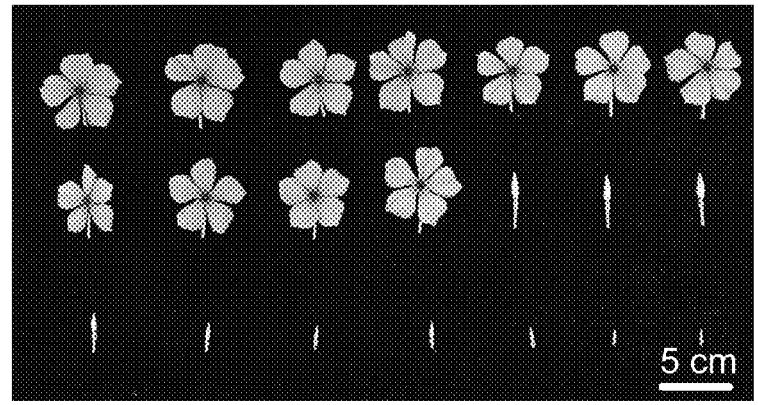
Figure 5A:
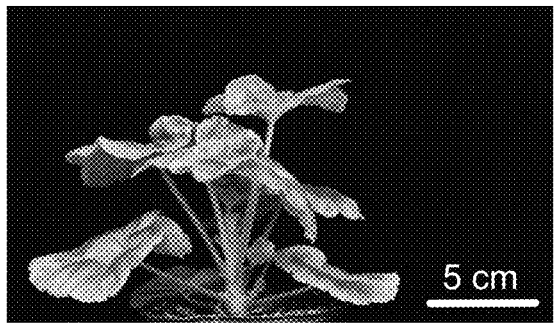
FIGS. 5A to 5D show phenotype observation of geranium one week after the second application of reagents in Example 2.
Figure 5B:
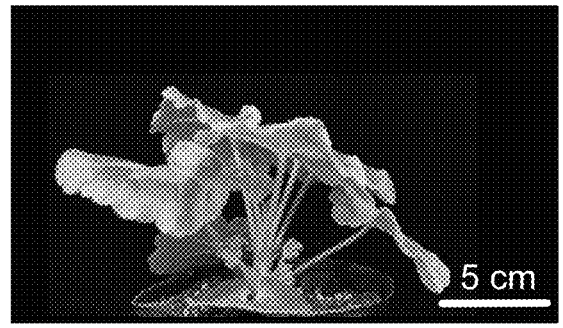
Figure 5C:
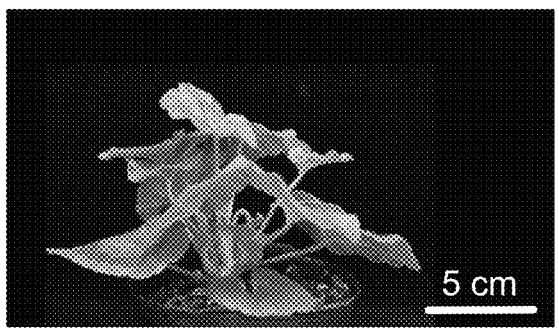
Figure 5D:
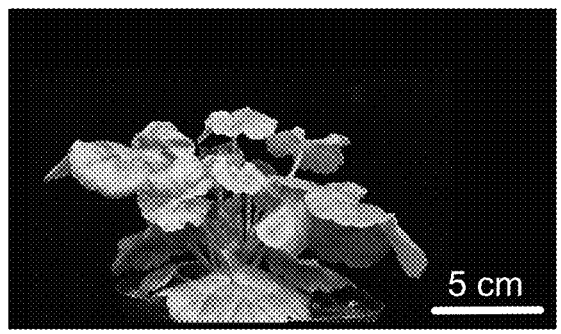

4.3 Total flower bud number: The flower bud morphology of Control group, Test groups 1-1, 1-2, and 1-3 are shown in FIGS. 3A, 3B, 3C, and 3D, respectively. Compared with plants of Control group (FIG. 3A), plants treated with GABA only (Test group 1-1, FIG. 3B), and plants treated with choline chloride and glutamic acid only (Test group 1-2, FIG. 3C), plants treated with the composition of the present invention (Test group 1-3, FIG. 3D) have more flowers and flower buds one week after the second application of reagents. In addition, as shown in FIG. 4, plants treated with the composition of the present invention (Test group 1-3) have greater total flower bud number than plants of Control group, plants treated with GABA only (Test group 1-1), and plants treated with choline chloride and glutamic acid only (Test group 1-2). There are significant differences between Test group 1-3 and Control group, between Test group 1-3 and Test group 1-1, and between Test group 1-3 and Test group 1-2 (p<0.05 or p<0.01).

The results above indicate that compared with Control group and treatment with GABA alone or choline chloride and glutamic acid only, the composition for regulating plant architecture of the present invention improves plant architecture, increases plant branches, and increases total numbers of flower and flower buds.

Example 2 Geranium Test

1. Preparation of Test Plants

Seedlings of geranium (*Pelargonium x hortorum*) (Known-You Seed Co., Ltd., Kaohsiung, Taiwan) were used as test plants in this example. Seeds of geranium were sown in pots containing culture medium (peat soil:vermiculite=3:1).

2. Plant Treatment

Geranium seedlings with three sets of unfolded true leaves were applied with the reagents listed in Table 4 twice with a two-week interval, using a foliar spray treatment. Plants in control group were applied with 0.1% (v/v) Tween® 80 in distilled water. The plants were kept in the phytotron for one more week after the second application of reagents for further analysis. Each group had 7 plants (n=7).

TABLE 4

Summary of the reagents applied to geranium in Example 2.

| Group | GABA (mg/L) | Glutamic acid (mg/L) | Choline chloride (mg/L) | Tween ® 80 |
|---|---|---|---|---|
| Control group | 0 | 0 | 0 | 0.1% (v/v) |
| Test group 2-1 | 100 | 0 | 0 | 0.1% (v/v) |
| Test group 2-2 | 0 | 400 | 300 | 0.1% (v/v) |
| Test group 2-3 | 100 | 400 | 300 | 0.1% (v/v) |

3. Analyses 3.1 Plant morphology: Plant morphology was observed one week after the second application of reagents.

3.2 Total branch number: The total branch number of each plant was calculated one week after the second application of reagents. This test was run in triplicate.

3.3 Average branch length: The average branch length of each plant was calculated one week after the second application of reagents. Branch length was defined as the distance from the mainstem to a growing point of a branch. The average branch length of a plant was calculated with the following equation. This test was run in triplicate.

Average branch length=(sum of branch lengths of a plant)/(total branch number of the plant).

3.4 Statistical analyses: Average and standard deviation (S.D.) of each group (n=7) were calculated. Statistically significant differences between control group and test groups were assessed by Student's T-test, where p-value<0.05 was considered a significant difference and indicated by an asterisk (*).

4. Results 4.1 Plant morphology: The plant morphology of Control group, Test groups 2-1, 2-2, and 2-3 are shown in FIGS. 5A, 5B, 5C, and 5D, respectively. Compared with plants of Control group (FIG. 5A), plants treated with GABA only (Test group 2-1, FIG. 5B), and plants treated with choline chloride and glutamic acid only (Test group 2-2, FIG. 5C), plants treated with the composition of the present invention (Test group 2-3, FIG. 5D) have significantly more branches and better plant architecture one week after the second application of reagents.

Figure 6:
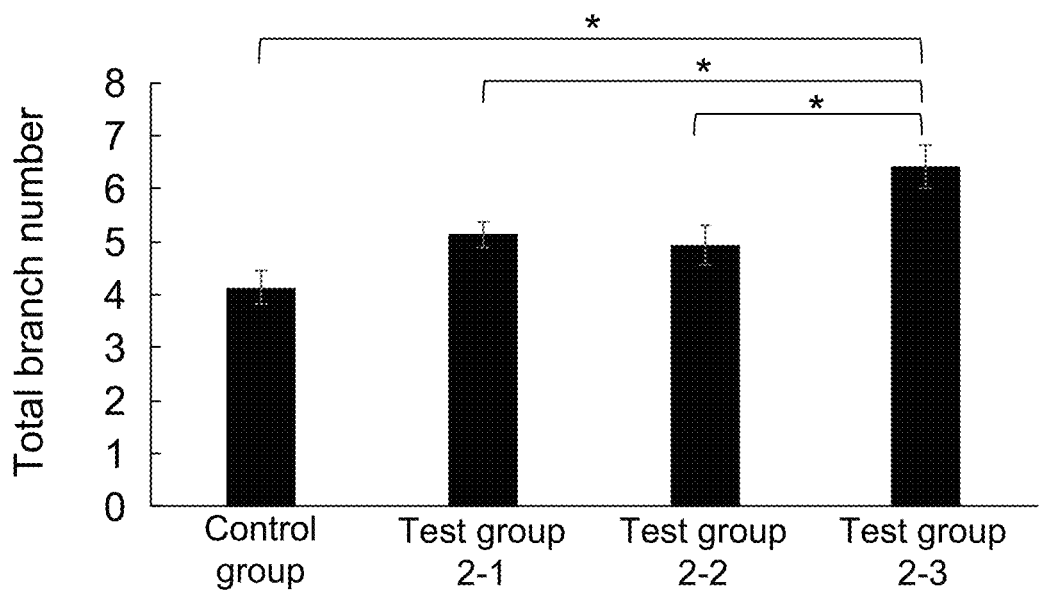
FIG. 6 shows the total branch numbers of geranium one week after the second application of reagents in Example 2. * $p<0.05$.

4.2 Total branch number: As shown in FIG. 6, plants treated with the composition of the present invention (Test group 2-3) have greater total branch number than plants of Control group, plants treated with GABA only (Test group 2-1), and plants treated with choline chloride and glutamic acid only (Test group 2-2). There are significant differences between Test group 2-3 and Control group, between Test group 2-3 and Test group 2-1, and between Test group 2-3 and Test group 2-2 (p<0.05).

Figure 7:
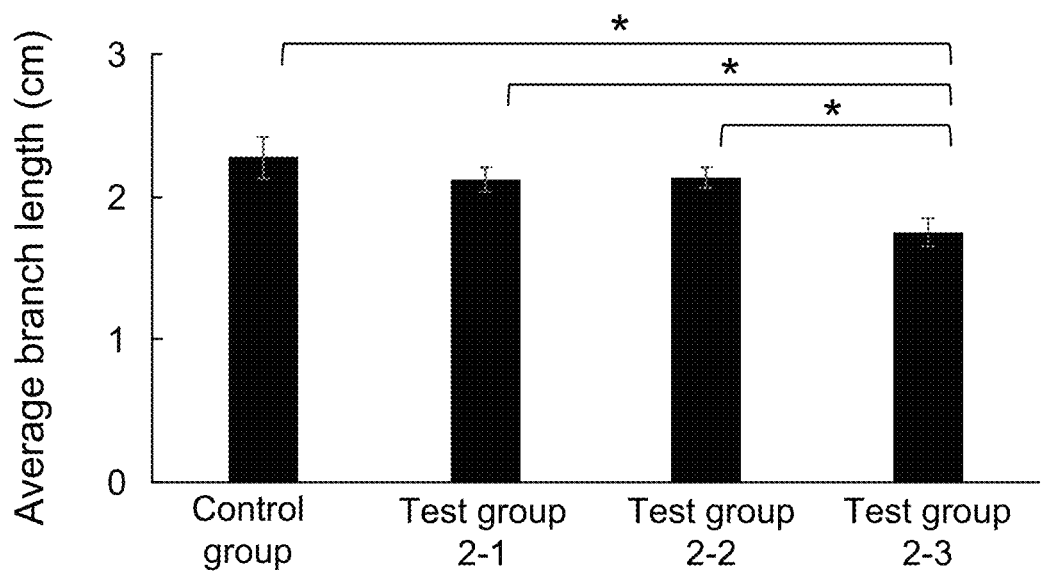
FIG. 7 shows the average branch lengths of geranium one week after the second application of reagents in Example 2. * $p<0.05$.

4.3 Average branch length: As shown in FIG. 7, plants treated with the composition of the present invention (Test group 2-3) have greater average branch length than plants of Control group, plants treated with GABA only (Test group 2-1), and plants treated with choline chloride and glutamic acid only (Test group 2-2). There are significant differences between Test group 2-3 and Control group, between Test group 2-3 and Test group 2-1, and between Test group 2-3 and Test group 2-2 (p<0.05).

The results above indicate that compared with Control group and treatment with GABA alone or choline chloride and glutamic acid only, the composition for regulating plant architecture of the present invention improves plant architecture, increases plant branches, and shorten branch lengths to dwarf plants.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A concentrate composition for regulating plant architecture, comprising
between about 5 to about 125 g/L γ-Aminobutyric acid (GABA);
between about 20 to about 200 g/L glutamic acid; and
between about 15 to about 375 g/L choline chloride.

2. The concentrate composition of claim 1, further comprising an adjuvant.

3. The concentrate composition of claim 2, wherein the adjuvant is a drift control agent.

4. The concentrate composition of claim 1, wherein the concentrate composition for regulating plant architecture is diluted about 200 to about 500 folds before use.

5. The concentrate composition of claim 1, wherein the concentrate composition for regulating plant architecture consists essentially of
between about 5 to about 125 g/L γ-Aminobutyric acid (GABA);
between about 20 to about 200 g/L glutamic acid; and
between about 15 to about 375 g/L choline chloride.

6. A ready to use composition for regulating plant architecture, comprising
between about 10 to about 625 mg/L γ-Aminobutyric acid (GABA);
between about 40 to about 2,500 mg/L glutamic acid; and
between about 30 to about 1,875 mg/L choline chloride.

7. The ready to use composition of claim 6, further comprising 0.01-1% (v/v) adjuvant.

8. The ready to use composition of claim 7, wherein the adjuvant is a surfactant.

9. The ready to use composition of claim 7, wherein the adjuvant is a drift control agent.

10. The ready to use composition of claim 6, wherein the ready to use composition for regulating plant architecture consists essentially of
between about 10 to about 625 mg/L γ-Aminobutyric acid (GABA);
between about 40 to about 2,500 mg/L glutamic acid; and
between about 30 to about 1,875 mg/L choline chloride.

11. A method for regulating plant architecture, comprising a step of applying a solution composition for regulating plant architecture to a plant, and the solution composition for regulating plant architecture comprising
between about 10 to about 625 mg/L γ-Aminobutyric acid (GABA);
between about 40 to about 2,500 mg/L glutamic acid; and
between about 30 to about 1,875 mg/L choline chloride.

12. The method of claim 11, wherein the solution composition for regulating plant architecture is applied to roots of the plant.

13. The method of claim 11, wherein the solution composition for regulating plant architecture is applied to a foliage of the plant.

14. The method of claim 11, wherein the solution composition for regulating plant architecture further comprises 0.01-1% (v/v) adjuvant.

15. The method of claim 14, wherein the adjuvant is a surfactant.

16. The method of claim 14, wherein the adjuvant is a drift control agent.

17. The method of claim 11, wherein the solution composition for regulating plant architecture increases a branch number of the plant.

18. The method of claim 11, wherein the solution composition for regulating plant architecture increases a total flower number of the plant.

19. The method of claim 11, wherein the solution composition for regulating plant architecture increases a total flower bud number of the plant.

20. The method of claim 11, wherein the solution composition for regulating plant architecture shortens branch lengths of the plant.

* * * * *